United States Patent [19] [11] 3,962,356
Holan [45] June 8, 1976

[54] SUBSTITUTED CYCLOPROPANES
[75] Inventor: George Holan, Brighton, Australia
[73] Assignee: Monsanto Chemicals Limited, Australia
[22] Filed: Aug. 15, 1974
[21] Appl. No.: 497,776

Related U.S. Application Data
[60] Division of Ser. No. 92,235, Nov. 23, 1970, Pat. No. 3,857,956, which is a division of Ser. No. 834,177, June 17, 1969, Pat. No. 3,642,910, which is a continuation-in-part of Ser. No. 684,554, Nov. 20, 1967, abandoned, which is a continuation of Ser. No. 402,949, Oct. 9, 1964, abandoned.

[30] Foreign Application Priority Data
Oct. 24, 1963   Australia............................ 36877/63

[52] U.S. Cl. .................. 260/649 R; 260/613 R; 424/353
[51] Int. Cl.$^2$.......................................... C07C 25/18
[58] Field of Search ..................... 260/649 R, 648 D

[56] References Cited
UNITED STATES PATENTS
3,642,910   2/1972   Holan............................ 260/649 R Primary Examiner—D. Horwitz
Attorney, Agent, or Firm—Richard H. Shear

[57] ABSTRACT 1,1-Di(p-substituted phenyl)-2,2-dichlorocyclopropanes, wherein the phenyl substituted are alkyl or alkoxy, as new compounds insecticides.

3 Claims, No Drawings

SUBSTITUTED CYCLOPROPANES

This application is a division of application Ser. No. 92,235, filed Nov. 23, 1970, now U.S. Pat. No. 3,857,956 which is in turn a division of application Ser. No. 834,177, now U.S. Pat. No. 3,642,910, which is a continuation-in-part of Ser. No. 684,554 filed Nov. 20, 1967, now abandoned which in turn is a continuation of application Ser. No. 402,949, filed Oct. 9, 1964, and now abandoned.

This invention relates to novel derivatives of 1,1-diphenyl-2,2-dichlorocyclopropane and to insecticidal compositions containing the derivatives of this invention as active ingredients.

The novel 1,1-diphenyl-2,2-chlorocyclopropane derivatives of this invention can be represented by the formula

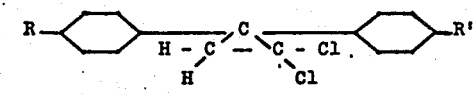

wherein R and R' are like or unlike and are hydrogen, alkyl groups containing from one to four carbon atoms inclusive, alkoxy groups containing from one to three carbon atoms inclusive, or a methylthio group, with not more than one of R and R' being hydrogen. The derivatives can be symmetrical with R and R' in the ortho, meta or para positions or combinations thereof. It is preferred, however, to utilize derivatives of the above type in which each ring is provided with a substituent in the para positions.

Representative dichlorocyclopropane derivatives of the present invention include, for example:

1-(p-methoxyphenyl)-1-(p-methoxyphenyl)-2,2-dichlorocyclopropane 1-(p-ethoxyphenyl)-1-(p-ethoxyphenyl)-2,2-dichlorocyclopropane 1-(p-propoxyphenyl)-1-(p-propoxyphenyl)-2,2-dichlorocyclopropane 1-(p-tolyl)-1-(p-tolyl)-2,2-dichlorocyclopropane 1-(p-ethylphenyl)-1-(p-ethylphenyl)-2,2-dichlorocyclopropane 1-(p-propylphenyl)-1-(p-propylphenyl)-2,2-dichlorocyclopropane 1-(p-butylphenyl)-1-(p-butylphenyl)-2,2-dichlorocyclopropane 1-(p-methoxyphenyl)-1-(p-ethoxyphenyl)-2,2-dichlorocyclopropane 1-(p-propoxyphenyl)-1-(p-tolyl)-2,2-dichlorocyclopropane 1-(p-methoxyphenyl)-1-(p-thiomethylphenyl)-2,2-dichlorocyclopropane 1-(p-ethoxyphenyl)-1-phenyl-2,2-dichlorocyclopropane and the like. Corresponding dichlorocyclopropanes in which one or both of the ring substituents are in the ortho or meta positions, are also within the scope of the present invention.

The new compounds of the present invention can be prepared by a number of methods involving reaction of an appropriate 1,1-diphenyl ethylene having the structural formula:

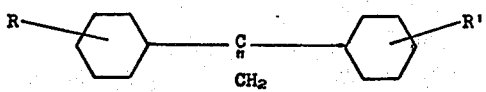

wherein R and R' are as defined above, in a medium which generates dichlorocarbene or which contains a dichloromethylene transfer agent. Thus, the 1,1-diphenyl ethylene can be reacted with a suitable phenyl(trihalomethyl)mercury, such as phenyl(trichloromethyl)mercury or phenyl(bromodichloromethyl)mercury, the bromodichloro compound reacting faster and more readily. The two reaction components can be mixed in any manner in an aprotic solvent and heated. Preferably, benzene is used as the solvent but other solvents such as chlorobenzene, dimethoxyethane, sulpholane, dimethylformamide, and the like, may be used. The temperature varies with the solvent, which should preferably boil above 50°C. The reaction is continued until substantially complete, usually requiring about 2 hours, but longer periods are not deleterious. Phenylmercuric chloride bromide is obtained as by-product, and can be removed by filtration or by any other convenient manner. The desired end product may be isolated by conventional means such as evaporation and filtration. Yields of almost 100% can be obtained.

The following non-limitative examples illustrate the preparation of the new compounds of the invention by reacting an appropriate 1,1-di-(p-substituted phenyl)ethylene with a suitable phenyl(trihalomethyl)mercury.

EXAMPLE 1

About 4.4 grams of bromodichloromethyl phenylmercury was added to a solution of about 2.54 grams of 1-(p-methoxyphenyl)-1-(p-ethoxyphenyl)ethylene in 50 ml. of benzene and the reaction mixture refluxed for approximately 10 hours. The solution was filtered to remove phenylmercuric bromide and then evaporated under reduced pressure. Recrystallization of the residue gave 1-(p-methoxyphenyl)-1-(p-ethoxyphenyl)-2,2-dichlorocyclopropane, m.p. 114°–117°C.

EXAMPLE 2

1-(p-Tolyl)-1-(p-tolyl)-2,2-dichlorocyclopropane, m.p. 115°C., was prepared by the procedure described in Example 1, using 1,1-di-(p-tolyl)-ethylene as a starting material.

EXAMPLE 3

Chloroform (0.2 moles) was added dropwise with stirring to a solution of 1,1-di-(p-methoxyphenyl)ethylene (0.1 mole) in methyl cyclohexane containing potassium tert-butoxide (0.4 moles) at 0°C. The mixture was allowed to warm to 20°C. overnight and then poured into water. The oil phase was separated and the solvent recovered. The residual solid was recrystallized from petroleum ether to give 1-(p-methoxyphenyl)-1-(p-methoxyphenyl)-2,2-dichlorocyclopropane, m.p. 141°C.

An alternative procedure for the preparation of the new compounds of this invention involves reaction of the appropriate 1,1-diphenylethylene with a haloform and a base. The haloform can be chloroform, bromodichloromethane, or the like, and the base preferably is potassium tert-butoxide. However, other bases such as butyl lithium, methyl lithium, and sodium hydride can be used. Other procedures involving systems which generate dichlorocarbene which can be used are the reaction of ethyl trichloroacetate and sodium methoxide; the decarboxylation of sodium trichloroacetate;

and the reaction of hexachloroacetone and a base, in each case the appropriate 1,1-diphenylethylene being included in the reaction system.

The appropriate 1,1-diphenylethylene starting material can be prepared by known methods such as from substituted phenyl magnesium bormide and ethyl acetate; or from methyl magnesium iodide and disubstituted benzophenone followed by dehydration; or from substituted acetophenone, as noted in Organic Syntheses Collective Volumes I, p. 221–222, 1932 Edition.

Compounds in accordance with the present invention are useful, inter alia, in controlling and combatting insect pests, particularly DDT-resistant insect pests such as DDT-resistant mosquitoes and flies and their larvae, as well as controlling and combatting insect pests in general, such as Southern Army worm, as hereinafter indicated. When DDT, more precisely 1,1,1-trichloro-2,2-bis(p-chlorophenyl)ethane, is used over an appreciable span of time in controlling or combatting insect colonies, strains of insects which are immune or resistant to the toxic effects of DDT are developed. Thus, DDT is ineffective against an ever-increasing proportion of the insect population. However, insect colonies do not develop an immunity or resistance to the insecticides of the present invention. It is surmised that an inability of insect life to effect dehydrochlorination of the above specified active compound is responsible for the unique activity of the above specified active compound against insect pests which have become DDT-resistant. Besides possessing the unique insecticidal activity indicated, it has been established that the above specified compounds also have a very low level of toxicity towards animals and a wide range of economic plants.

In controlling and combatting insect pests according to the present invention, any of the compounds of this invention either per se or insecticidal compositions comprising any of said compounds are applied to the insect pests or to their environment in a lethal or toxic amount. This can be done by distributing the compounds or insecticidal compositions, containing them in or about an infested environment or in or about an environment which the insect pests frequent, e.g. agricultural soil or other growth media or other media attractive to the pests for habitational, sustenance or propagational purposes, in any conventional fashion which permits the insect pests to be subject to the insecticidal action of the compounds. Such distribution can be brought about by applying sprays or particulate solid compositions to a surface infested with the insect pests or attractable to the pests, as for example, the surface of an agricultural soil or other habitat media such as the above-ground surface of host plants by any of the conventional methods, e.g. powder dusters, boom and hand sprayers, and spray dusters. Also for sub-surface application such distribution can be carried out by simply mixing the compounds or insecticidal spray or particulate solid composition comprising same with the infested environment or with the environment the insect pests frequent, or by employing a liquid carrier for the compounds to accomplish sub-surface penetration and impregnation therein.

Thus, although the present compounds are useful per se in controlling and combatting insect pests, it is preferable in practicing the present invention, that they be applied to the pests or to the environment of the pests dispersed in a suitable extending agent. The dispersion of the compounds can be accomplished in various ways. Thus, the particles can be molecular in size and held in true solution in a suitable solvent or colloidal in size and distributed throughout a liquid phase in the form of suspensions or emulsions with or without surface-active agents of a non-ionizing character. Also the particles can be distributed in a semi-solid viscous carrier such as petroleum or other ointment base of a non-ionizing character in which they may be actually dissolved in the semi-solid or held in suspension in the semi-solid with the aid of suitable non-ionizing surface-active agents. Alternately, the particles may be mixed with and distributed throughout a solid carrier providing a mixture in particulate form, e.g. pellets, granules, powders, or dusts. In addition, the particles can be in mixtures which are suitable for use as aerosols including solutions, suspensions, or emulsions in carriers such as dichlorodifluoromethane and like haloalkanes or mixtures thereof and/or with other substances which boil below room temperature at atmospheric pressure. In this specification the expression "extending agent" includes any and all of those substances in which the compound is dispersed, including the solvents of a true solution, the liquid phase of suspensions, emulsions or aerosols, the semi-solid carrier of ointments, and the solid phase of particulate solids, e.g. pellets, granules, dusts and powders.

The concentration of the compounds employed according to the invention in controlling and combatting insect pest can vary considerably provided that a toxic or lethal amount thereof is supplied to the pests or to the environment of the pests. When the extending agent is a liquid or mixture of liquids, as in solutions, suspensions, emulsions, or aerosols, the concentration of the compound employed to supply the required dosage is in the general range of about 0.001 to about 50 per cent by weight of the total composition. When the extending agent is a semi-solid or solid, the concentration of the compounds employed to supply the desired dosage is in the general range of about 0.01 to about 25 percent by weight of the formulation.

A large number of organic liquids can be used for the preparation of solutions, suspensions or emulsions of the compound. Suitable organic liquids include, for example, isopropyl ether, acetone, methyl ethyl ketone, octanone, dioxane, cyclohexanone, carbon tetrachloride, ethylene dichloride, tetrachloroethane, hexane, heptane, and like higher liquid alkanes, hydrogenated naphthalenes, solvent naphtha, benzene, toluene, xylene, petroleum fractions such as kerosene and the like boiling almost entirely under about 400°F., and having a flash point above about 80°F., mineral oils having an unsulfonatable residue above about 80 per cent and preferably above about 90 per cent and the like. In those instances wherein there may be concern about the phytotoxicity of the organic liquid extending agent, a portion thereof can be replaced by low molelcular weight aliphatic hydrocarbons such as dipentene, diisobutylene, propylene trimer, and the like or suitable polar organic liquids such as the aliphatic ethers and the aliphatic ketones containing not more than about 10 carbon atoms as exemplified by acetone, methyl ethyl ketone, diisobutyl ketone, dioxane, isopropyl ether, and the like. In certain instances, it is advantageous to employ a mixture of organic liquids as the extending agent, e.g. an aromatic hydrocarbon and an aliphatic ketone.

The dichlorocyclopropane derivatives of this invention are preferably applied to the insect pests or to their environment in the form of emulsions or suspensions prepared by dispersing the derivatives or solutions thereof in water with the aid of a water-soluble non-ionic surfactant. The term "surfactant" as employed in this specification is used as in Volume II of Schwartz, Perry and Berch's "Surfact Active Agents and Detergents" (1958, Interscience Publishers, Inc., New York) in place of the expression "emulsifying agent", to connote generically the various "emulsifying agents", "dispersing agents", "wetting agents" and "spreading agents" that are adapted to be admixed with the said derivatives in order to secure better wetting and spreading of the active ingredient in the water vehicle or carrier in which they are insoluble (see also Frear "Chemistry of Insecticides, Fungicides and Herbicides", second edition, page 280). The surfactants contemplated are the well-known capillary active substances which are non-ionizing (or non-ionic) and which are described in detail in Volumes I and II and Schwartz, Perry and Berch's "Surface Active Agents and Detergents", (1958, Interscience Publishers, Inc., New York) and also in the November 1947 issue of Chemical Industries (pages 811–824) in an article entitled "Synthetic Detergents" by John W. McCutcheon and also in the July, August, September and October, 1952 issues of Soap and Sanitary Chemicals under the title "Synthetic Detergents". The disclosures of these articles with respect to non-ionizing capillary active substances are incorporated in this specification by reference in order to avoid unnecessary enlargement of this specification. The preferred surfactants are the water-soluble non-ionic surface-active agents set forth in U.S. Pat. No. 2,846,398, issued Aug. 5, 1958 to Beaver and Stoffel.

The present insecticides can be dispersed by suitable procedures (e.g. tumbling or grinding) in organic or inorganic solid extending agents and applied in particulate form to the insect pests or their environment. Such solid materials include for example, tricalcium phosphate, calcium carbonate, kaolin, bole, kieselguhr, talc, bentonite, fuller's earth, pyrophillite, diatomaceous earth, calcined magnesia, volcanic ash, sulfur, powdered cork, powdered wood, and powdered walnut shells, and the like. While a large variety of solid carriers are suitable, it is preferred to use absorbent clays such as bentonite. These mixtures can be used for insecticidal purposes in the dry form. Alternately, by addition of water-soluble non-ionic surfactants the dry particulate solids can be rendered wettable by water and readily convertible to stable aqueous dispersions or suspensions suitable for use as sprays. For special purposes the present insecticidal compounds can be dispersed in a semi-solid extending agent such as petrolatum with or without the aid of solubility promoters and/or non-ionic surfactants.

A concentrate, for example, in the form of a spray base or particulate solid base is provided in such form that, by merely mixing with water or with a solid extender such as powdered clay, or talcs, or other low-cost readily-available material, an easily prepared spray or particulate solid insecticide for household or agricultural purpose is produced. In such a concentrate composition, the above specified active compounds are generally present in a concentration of 5 to 95 per cent by weight, the residue being any one or more of the well-known insecticidal adjuvants, such as the surface-active clays, solvents, diluents, carrier media, adhesives, spreading agents, humectants, and the like.

A particularly useful concentrate ready for mixing with or dispersing in other extending agents is an intimate mixture of the present compounds with a wetting and dispersing agent in proportions of about 0.1 to about 20 parts of surfactant with an amount of the dichlorocyclopropanes to provide 100 parts by weight. Such a concentrate is particularly well adapted to be made into a spray for combatting various forms of insect pests by the addition of water thereto. As illustrative of such a concentrate is an intimate mixture of about 80 parts by weight of 1-(p-methoxyphenyl)-1-(p-ethoxyphenyl)-2,2-dichlorocyclopropane and about 20 parts by weight of a wetting or dispersing agent. Another useful concentrate adapted to be made into a spray for combatting insect pests is a solution of one or more of the compounds of the present invention in an organic solvent containing a minor amount of an emulsifying agent. As illustrative of such a concentration is a solution of 1-(p-methoxyphenyl)-1-(p-ethoxyphenyl)-2,2-dichlorocyclopropane in solvent naphtha, xylene or a petroleum fraction such as kerosene, containing an emulsifying agent.

In all of the various dispersions described hereinbefore for insecticidal purposes, the active ingredients can be advantageously employed in combination with other pesticides, including for example, other insecticides, nematocides, bactericides, and herbicides. In this manner it is possible to obtain mixtures which are effective against a wide variety of pests and other forms of noxious life.

Insecticidal activity of the compounds of the present invention was demonstrated by a series of tests against mosquito larvae specie *Aedes aegypti*, adult female house flies, Mexican bean beetle larvae and Southern army worms. The compounds used in this series of tests were:

A    1-(p-methoxyphenyl)-1-(p-ethoxyphenyl)-2,2-dichlorocyclopropane
B    1-(p-tolyl)-1-(p-tolyl)-2,2-dichlorocyclopropane
C    1-(p-methoxyphenyl)-1-(p-methoxyphenyl)-2,2-dichlorocyclopropane
D    1-(p-propoxyphenyl)-1-(p-propoxyphenyl)-2,2-dichlorocyclopropane
E    1-(p-ethylphenyl)-1-(p-ethylphenyl)-2,2-dichlorocyclopropane
F    1-(p-ethoxyphenyl)-1-(-ethoxyphenyl)-2,2-dichlorocyclopropane The test procedure for mosquito larvae was as follows: A rimless 25 × 200 culture tube was rinsed with acetone and was placed in a holding block. The tube was filled with 70 cc of distilled water. Then 0.1 cc of liquid or 0.1 g of the solid test compound was dissolved in acetone to make a 1% by weight concentrate of the test chemical. 0.007 ml of this concentrate was pipetted into the culture tube containing the distilled water. The tube was then stoppered with an acetone washed rubber stopper and shaken to facilitate complete mixing. Approximately 25 early fourth instar yellow fever mosquito larvae *Aedes aegypti* were transferred to the tube with the aid of a pipette. The larvae were held in the test tube at room temperature for 24 hours at which time mortality observations were taken. Any larvae capable of any movement were considered to be alive.

The following results were obtained:

| Compound | Concentration | Percent Kill |
|---|---|---|
| A | 0.2 ppm | 80 |
| B | 2.0 ppm | 100 |

| Compound | -continued Concentration | Percent Kill |
|---|---|---|
| D | 1.0 ppm | 100 |
| E | 2.0 ppm | 100 | inches high, 5 inches in diameter and faced on top and bottom with 14 mesh screen. The spray procedure was repeated with solutions of different concentrations of each compound and with other insects as indicated to determine optimum concentrations of the various compounds.

| Compound | Insect | Concentration | Percent Kill 24 hrs. | 48 hrs. |
|---|---|---|---|---|
| A | House Flies | 0.1% | 94 | |
| A | " | 0.05% | 54 | |
| D | " | 0.01% | 100 | |
| E | " | 0.1% | 100 | |
| E | " | 0.05% | 96 | |
| F | " | 0.001% | 50 | |
| E | Southern Army Worms | 0.1% | 100 | |
| A | Mexican bean beetle larvae | 0.05% | | 100 |
| A | " | 0.01% | | 90 |
| A | " | 0.005% | | 70 |
| C | " | 0.05% | | 80 |
| E | " | 0.05% | | 100 |
| E | Pea aphids | 0.1% | 100 | |
| E | " | 0.05% | 50 | |

A topical test was used to illustrate the insecticidal activity of compounds of the present invention against house flies and Southern army worms. In this test, female house flies, two to three days of age, were anaesthesized with gaseous $CO_2$ and picked up individually by a wing with forceps. A one-microlitre drop of solution of chemical was placed on a fly (dorsum of the prothorax). Ten flies were used per replicate per dose level. Treated flies were placed in half-pint cartons covered with a screen wire top. Liquid food was provided during the post-treatment period. Flies were held at the existing laboratory temperatures and relative humidity. Observations for mortality were made 24 hours after treatment. Flies incapable of performing normal walking and flying movements were considered to be dead.

The results of this test are given below. With the exception of one test for Compound D marked with an asterisk and directed to Southern army worms, the results are based on work with house flies. Concentration is given in micrograms per insect.

| Compound | Concentration | Percent Kill |
|---|---|---|
| A | 1 | 100 |
| B | 1 | 60 |
| C | 1 | 80 |
| D | 10 | 100 |
| D* | 1 | 70 |
| E | 10 | 100 |
| F | 0.2 | 50 |

In addition, the effectiveness of the present compounds was shown by subjecting insects to sprays of solutions of the compounds. Samples of each compound were formulated by dissolving the compounds in acetone and adding a small amount of emulsifier and water. The formulated samples were applied to house flies in a contact test in a vertical spray tower, operating at about 10 psi and discharging about 28 milliliters of solution per minute through a glass atomizer. The spray descended through a stainless steel cylinder 8 inches in diameter to the test house flies about 44 inches below the atomizer. During the spraying operation, which was maintained with each sample for a period of about ten seconds, a colony of fifty adult house flies were retained in a cylindrical stainless steel cage positioned within the spray tower. The cage was 2 inches high, 5 inches in diameter and faced on top and bottom with 14 mesh screen. The spray procedure was repeated with solutions of different concentrations of each compound and with other insects as indicated to determine optimum concentrations of the various compounds.

It will be understood that the terms "insect" and "insecticide" are used herein in their broad common usage to include spiders, mites, ticks, and like pests which are not in the strict biological sense classed as insects. Thus the usage therein conforms to the definitions provided by Congress in Public Law 104, the "Federal Insecticide, Fungicide, and Rodenticide Act" of 1947, Section 2, subsection h, wherein the term "insect" is used to refer not only to those small invertebrate animals belonging mostly to the class Insecta, comprising six-legged, usually winged forms, as beetles, bugs, bees, flies, and so forth, but also to other allied classes of arthropods whose members are wingless and usually have more than six legs, as spiders, mites, ticks, centipedes, and wood lice.

While the invention has been described in considerable detail with reference to specific embodiments thereof, other modifications and variations will suggest themselves to those skilled in the art.

We claim:
1. A compound of the formula

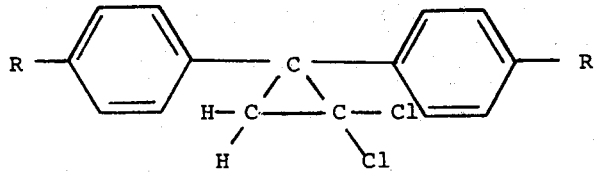

wherein R and R' are selected from the group consisting of alkyl groups containing from 1 to 4 carbon atoms inclusive.

2. A compound of claim 1 which is 1-(p-tolyl)-1(p-tolyl)-2,2-dichlorocyclopropane.

3. A compound of claim 1 which is 1-(p-ethylphenyl)-1-(p-ethylphenyl)-2,2-dichlorocyclopropane.

* * * * *

UNITED STATES PATENT OFFICE
CERTIFICATE OF CORRECTION

Patent No. 3,962,356                Dated   June 8, 1976

Inventor(s)  George Holan

It is certified that error appears in the above-identified patent and that said Letters Patent are hereby corrected as shown below:

In the Abstract: line 2, "substituted" should read -- substituents --; line 3, after "compounds" insert -- and --.

Claim 1, the formula should read:

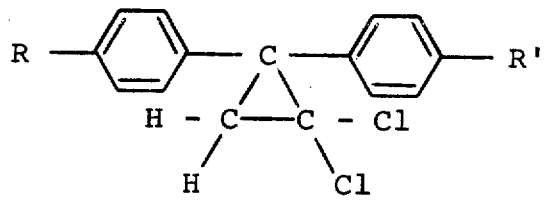

Signed and Sealed this

Twenty-eighth Day of December 1976

[SEAL]

Attest:

RUTH C. MASON
*Attesting Officer*

C. MARSHALL DANN
*Commissioner of Patents and Trademarks*